(12) United States Patent      (10) Patent No.: US 8,968,392 B2
Omura et al.      (45) Date of Patent: Mar. 3, 2015

(54) METHOD OF INHIBITING VASCULAR INTIMAL HYPERPLASIA USING STENT

(75) Inventors: Ikuo Omura, Okayama (JP); Zhen Yu Jin, Okayama (JP); Shuzo Yamashita, Okayama (JP); Hiroo Iwata, Kyoto (JP); Akira Mochizuki, Numazu (JP)

(73) Assignees: Japan Stent Technology Co., Ltd., Okayama (JP); Tokai University Educational System, Tokyo (JP); Toyo Advanced Technologies Co., Ltd., Hiroshima (JP); Hiroo Iwata, Kyoto (JP)

( * ) Notice: Subject to any disclaimer, the term of this patent is extended or adjusted under 35 U.S.C. 154(b) by 389 days.

(21) Appl. No.: 13/561,828

(22) Filed: Jul. 30, 2012

(65) Prior Publication Data

US 2013/0018455 A1    Jan. 17, 2013

Related U.S. Application Data

(60) Division of application No. 12/733,460, filed on Mar. 3, 2010, now Pat. No. 8,409,272, which is a continuation of application No. PCT/JP2008/002410, filed on Sep. 3, 2008.

(30) Foreign Application Priority Data

Sep. 4, 2007    (JP) ................................ 2007-228788

(51) Int. Cl.
*A61F 2/82*      (2013.01)
*A61F 2/00*      (2006.01)
(Continued)

(52) U.S. Cl.
CPC . *A61F 2/82* (2013.01); *A61F 2/915* (2013.01); *A61K 9/0024* (2013.01); *A61L 31/10* (2013.01);
(Continued)

(58) Field of Classification Search
None
See application file for complete search history.

(56) References Cited

U.S. PATENT DOCUMENTS 7,033,602 B1    4/2006    Pacetti et al. ................ 424/426
7,179,285 B2    2/2007    Ikeuchi et al.
(Continued)

FOREIGN PATENT DOCUMENTS

CN      1568166 A      1/2005
CN      1925881 A      3/2007
(Continued)

OTHER PUBLICATIONS

Japanese Office Action issued May 21, 2013 in related Japanese Application No. 2009-531112.
(Continued)

*Primary Examiner* — Jeffrey T Palenik

(57) ABSTRACT

A method of inhibiting vascular intimal hyperplasia including: placing a stent within a blood vessel, the stent having a stent body of a cylindrical configuration having outer and inner surfaces with a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer; and causing argatroban to be released from the stent to thereby inhibit the vascular intimal hyperplasia without inhibiting proliferation of endothelial cells.

26 Claims, 2 Drawing Sheets

Stent1

(51) Int. Cl.
*A61L 33/00* (2006.01)
*A61F 2/915* (2013.01)
*A61K 9/00* (2006.01)
*A61L 31/10* (2006.01)
*A61L 31/16* (2006.01)
*A61F 2/91* (2013.01)

(52) U.S. Cl.
CPC . *A61L 31/16* (2013.01); *A61F 2/91* (2013.01); *A61F 2002/91541* (2013.01); *A61F 2250/0067* (2013.01); *A61L 2300/416* (2013.01); *A61L 2300/608* (2013.01); *A61L 2420/08* (2013.01)
USPC .......... 623/1.46; 424/423; 424/424; 424/425; 424/426; 427/2.25

(56) References Cited

U.S. PATENT DOCUMENTS

| | | | |
|---|---|---|---|
| 7,229,471 B2 | 6/2007 | Gale et al. | |
| 7,357,942 B2 | 4/2008 | Burke et al. | |
| 7,378,105 B2 | 5/2008 | Burke et al. | |
| 7,625,399 B2 | 12/2009 | Case et al. | |
| 7,691,401 B2 | 4/2010 | Castro et al. | 424/426 |
| 7,985,251 B2 | 7/2011 | Ikeuchi et al. | |
| 8,157,857 B2 | 4/2012 | Case et al. | |
| 8,221,495 B2 | 7/2012 | Shrivastava et al. | |
| 2002/0168393 A1 | 11/2002 | Sugimoto | |
| 2003/0158596 A1 | 8/2003 | Ikeuchi et al. | |
| 2004/0034409 A1 | 2/2004 | Heublein et al. | |
| 2004/0117007 A1 | 6/2004 | Whitbourne et al. | |
| 2005/0015136 A1 | 1/2005 | Ikeuchi et al. | |
| 2005/0060028 A1 | 3/2005 | Horres et al. | |
| 2005/0176678 A1 | 8/2005 | Horres et al. | |
| 2006/0036311 A1 | 2/2006 | Nakayama et al. | |
| 2006/0093771 A1 | 5/2006 | Rypacek et al. | |
| 2007/0141112 A1 | 6/2007 | Falotico et al. | |
| 2008/0038307 A1 | 2/2008 | Hoffmann | |
| 2009/0005861 A1 | 1/2009 | Hossainy et al. | 623/1.46 |
| 2009/0005862 A1 | 1/2009 | Nakatani et al. | 623/1.49 |
| 2009/0048667 A1 | 2/2009 | Mochizuki et al. | |
| 2010/0249914 A1 | 9/2010 | Omura et al. | 623/1.46 |
| 2011/0060403 A9 | 3/2011 | Nakatani et al. | 623/1.49 |

FOREIGN PATENT DOCUMENTS

| | | |
|---|---|---|
| JP | 7-196650 | 8/1995 |
| JP | 11-500047 | 1/1999 |
| JP | 2001-190687 | 7/2001 |
| JP | 2002-000739 | 1/2002 |
| JP | 2003-24452 | 1/2003 |
| JP | 2003-024452 | 1/2003 |
| JP | 2003-33439 | 2/2003 |
| JP | 2003-190294 | 7/2003 |
| JP | 2004-267368 | 9/2004 |
| JP | 2004-526499 | 9/2004 |
| JP | 3605388 | 10/2004 |
| JP | 3654627 | 3/2005 |
| JP | 2005-170801 | 6/2005 |
| JP | 2005-516736 | 6/2005 |
| JP | 2005-530551 | 10/2005 |
| JP | 2005-534724 | 11/2005 |
| JP | 2007-190369 | 8/2007 |
| JP | 2007-195883 | 8/2007 |
| JP | 2007-215620 | 8/2007 |
| JP | 2007-229123 | 9/2007 |
| JP | 2008-523901 | 7/2008 |
| JP | 2008-179788 | 8/2008 |
| WO | WO 97/10011 | 3/1997 |
| WO | 00/15271 | 3/2000 |
| WO | WO 02/074194 A2 | 9/2002 |
| WO | 02/080996 A1 | 10/2002 |
| WO | WO 03/068289 A1 | 8/2003 |
| WO | 04/000379 A1 | 12/2003 |
| WO | 2004/022150 A1 | 3/2004 |
| WO | 2005/097224 A1 | 10/2005 |
| WO | 2006/065685 A | 6/2006 |
| WO | WO 2007/032777 A2 | 3/2007 |
| WO | WO 2007/047473 A2 | 4/2007 |
| WO | 2007/058190 A1 | 5/2007 |
| WO | WO 2007/086269 A1 | 8/2007 |
| WO | WO 2007/148714 A1 | 12/2007 |
| WO | WO 2009/031295 A1 | 3/2009 |

OTHER PUBLICATIONS

Extended European Search Report issued May 24, 2013 in related European Application No. 08829751.0.
U.S. Office Action mailed Feb. 27, 2013 in U.S. Appl. No. 13/137,560.
U.S. Office Action mailed May 17, 2013 in U.S. Appl. No. 13/492,290.
Chinese Office Action mailed Mar. 22, 2013 in corresponding Chinese Application No. 200880105243.4.
Chinese Office Action mailed Apr. 7, 2013 in corresponding Chinese Application No. 201010267157.2.
Leila Mureebe et al, "Inhibition of Intimal Hyperplasia by Direct Thrombin Inhibitors in an Animal Vein Bypass Model", Annals of Vascular Surgery, Aug. 2004, pp. 147-150.
Japanese Office Action mailed Nov. 12, 2013 in a related Japanese Patent Application No. 2011-502731.
Chinese Office Action mailed Oct. 8, 2013 in a related Chinese Patent Application No. 20080105243.4.
Chinese Office Action mailed Oct. 17, 2013 in a related Chinese Patent Application No. 201010267157.2.
Chinese Office Action issued Jul. 20, 2012 in corresponding Chinese Patent Application No. 200880105243.4.
Australian Patent Examination Report No. 1 issued Jul. 12, 2012 in corresponding Australian Patent Application No. 2010202640.
Australian Patent Examination Report No. 1 issued Jun. 21, 2012 in corresponding Australian Patent Application No. 2008294278.
Notice of Allowance mailed from the United States Patent and Trademark Office on Sep. 30, 2013 in U.S. Appl. No. 13/492,290.
Notice of Allowance mailed from the United States Patent and Trademark Office on Jul. 24, 2013 in U.S. Appl. No. 13/137,560.
Japanese Notification of Reasons for Rejection issued Dec. 11, 2012, in corresponding Japanese Patent Application No. 2010-134943.
Chinese Office Action issued Nov. 29, 2012, in corresponding Chinese Patent Application No. 201010267157.2.
U.S. Notice of Allowance mailed Sep. 6, 2012, issued in parent U.S. Appl. No. 12/733,460.
U.S. Office Action issued Mar. 18, 2014, in U.S. Appl. No. 13/729,630.
Chinese Office Action issued Mar. 26, 2014, in related Chinese Patent Application 201010267157.2.
European Office Action issued May 21, 2014, in related European Patent Application No. 08 829 751.0.
U.S. Appl. No. 13/137,560, filed Aug. 25, 2011, Ikuo Omura et al, Japan Stent Technology Co., Ltd.
U.S. Appl. No. 13/729,630, filed Dec. 28, 2012, Ikuo Omura et al, Japan Stent Technology Co., Ltd.
Japanese Office Action mailed Feb. 4, 2014 in corresponding Japanese Application No. 2013-021872.
Japanese Office Action mailed Feb. 4, 2014 in corresponding Japanese Application No. 2013-021873.
Kayla L. Metzger et al., Pharmacokinetic and behavioral characterization of a long-term antipsychotic delivery system in rodents and rabbits, Psychlpharmacology, DOI 10.1007/s0023-006-0616-8, Received: May 31, 2006/Accepted: Oct. 13, 2006 © Springer-Verlag 2006, pp. 1-11.
English Translation of the International Preliminary Report on Patentability mailed Apr. 8, 2010 in corresponding International Patent Application PCT/JP2008/002410.
International Search Report for PCT/JP2008/002410, mailed Oct. 7, 2008.
Office Action mailed from the Unites States Patent and Trademark Office on Sep. 30, 2011 in the related U.S. Appl. No. 12/733,460.

(56) References Cited

OTHER PUBLICATIONS

Communication mailed from the Unites States Patent and Trademark Office on Jan. 11, 2012 in the related U.S. Appl. No. 12/733,460.
Restriction Requirement mailed from the Unites States Patent and Trademark Office on Apr. 19, 2012 in the related U.S. Appl. No. 12/733,460.
Office Action mailed from the Unites States Patent and Trademark Office on Sep. 12, 2011 in the related U.S. Appl. No. 12/801,307.
U.S. Appl. No. 12/733,460, filed Mar. 3, 2010, Ikuo Omura et al., Japan Stent Technology Co., Ltd., Tokai University Educational System, Toyo Advanced Technologies Co., Ltd. and Hiroo Iwata of Kyoto-Shi, Japan.
U.S. Appl. No. 12/801,307 (Abandoned), filed Jun. 2, 2010, Ikuo Omura et al., Japan Stent Technology Co., Ltd., Tokai University Educational System, and Hiroo Iwata of Kyoto-Shi, Japan.
U.S. Appl. No. 13/492,290, filed Jun. 8, 2012, Ikuo Omura et al., Japan Stent Technology Co., Ltd., Tokai University Educational System, Toyo Advanced Technologies Co., Ltd. and Hiroo Iwata of Kyoto-Shi, Japan.
Korean Office Action issued Aug. 22, 2014 in related Korean Patent Application No. 10-2010-7007202.
Korean Office Action issued Aug. 28, 2014 in related Korean Patent Application No. 10-2010-7013253.
Japanese Office Action issued Sep. 30, 2014 in related Japanese Patent Application No. 2013-021872.
Extended European Search Report issued Jul. 30, 2014 in related European Patent Application No. 10164082.9.

Stent1

2.0 mm

HISTOPATHOLOGICAL SAMPLE OF DES 2

2.0 mm

HISTOPATHOLOGICAL SAMPLE OF DES 5

METHOD OF INHIBITING VASCULAR INTIMAL HYPERPLASIA USING STENT

CROSS-REFERENCE TO RELATED APPLICATIONS

This application is a divisional of U.S. patent application Ser. No. 12/733,460, filed Mar. 3, 2010, now U.S. Pat. No. 8,409,272, which is a continuation application, under 35 U.S.C. §111(a), of international application No. PCT/JP2008/002410, filed Sep. 3, 2008, which claims priority to Japanese patent application No. 2007-228788, filed Sep. 4, 2007, the disclosures of which are incorporated by reference in their entirety into this application.

BACKGROUND

1. Field

The present invention relates to a sustained drug-releasing stent useful for treatment of a constricted blood vessel, a method of making the same and a method of controlling the rate of release of the sustained release drug from the stent. More specifically, the present invention relates to a stent carrying a vascular intimal hyperplasia inhibitor, which does not inhibit proliferation of endothelial cells, a method of making such stent and a method of controlling the rate of release of the inhibitor from the stent.

2. Description of the Related Art

In recent years, the stent treatment is getting popular in the field of medical treatment, in which an affected area of the coronary artery having been constricted as a result of progress of arteriosclerosis is mechanically expanded with the aid of a balloon catheter, followed by placement of a metallic stent within the vascular lumen to restore the flow of blood. Development of the stent treatment is indeed a good news to patients suffering from arterial stenosis. However, placement of such a stent in the coronary artery, of which constriction or occlusion is highly fatal, has been found involving the probability of postoperative treatment required reaches 20 to 30% because even though the stent has been placed, vascular intimal hyperplasia occurs with the vascular lumen narrowed consequently. In view of the above, in order to decrease the in-stent restenosis, attempts have been made to design a stent of a type having its surface carrying a drug effective to exhibit restenosis prevention effects so that the drug, when the stent is placed in an artery, can be released in a controlled manner within the vascular lumen to thereby suppress the restenosis. Those attempts have led to commercialization of drug releasing stents (hereinafter referred to as DES) utilizing sirolimus (immunosuppresssor) and paclitaxel (anticancer drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation of the endothelial cells once denuded during placement of the stent is also suppressed, resulting in an adverse effect of the repair or treatment of the inner wall of a blood vessel being retarded. In view of the fact that thrombosis tends to occur easily at the site of the inner wall of a blood vessel that are not covered with endothelial cells, an antithrombotic drug must be administrated for a prolonged time, say, half a year or so and, even though the antithrombotic drug is administrated, there is a risk that the late thrombosis may result in accompanied by a sudden death.

The first event occurring in the causal sequence from the intravascular stent placement to the in-stent restenosis is said to be an "injury to the blood vessel at the time of placement of the stent, particularly an injury to the endothelial cells", which leads to a causal consequence of "formation of blood clots", "adhesion or infiltration of leukocytes into the blood wall", "inflammation", "proliferation of smooth muscle cells" and "stenosis" in this order. Accordingly, it is expected that suppression of the formation of blood clots is effective to inhibit the stenosis and, based on this view, application of an antithrombotic drug such as, for example, heparin or hirudin to form a drug releasing stent has been strenuously tried at the initial stage of development thereof, but the clinical effectiveness thereof has not been ascertained. Now that the drug releasing stent utilizing sirolimus or paclitaxel has been widespread in these days, the drug releasing stent coated with the antithrombotic drug has been minor candidate in the development of drug releasing stents. At present, however, no drug releasing stent capable of accomplishing a sustained release of a vascular intimal hyperplasia inhibitor, which is free from injury to the endothelial cells, has yet been made available.

On the other hand, the Patent Document 1 listed below discloses in an embodiment of the invention thereof, a stent capable of releasing both of argatroban (anticoagulant agent) and cilostazol (antiplatelet agent). The Patent Document 2 also listed below discloses the rate of release of the drug from a polymer film containing argatroban, immersed in a solution of phosphate buffer (pH 7.4) for three weeks. In any event, however, no surprising effect of inhibiting the vascular intimal hyperplasia while the drug is carried by the stent has yet been observed.

[Patent Document 1] JP Laid-open Patent Publication No. 2001-190687
[Patent Document 2] WO2007/058190

SUMMARY

An object of the present invention is to provide a stent carrying a vascular intimal hyperplasia inhibitor of a kind, which does not inhibit proliferation of endothelial cells, which stent is capable of releasing the drug in controlled manner, and a method of making such stent.

Another important object of the present invention is to provide a method of controlling the rate of release of the drug from the stent carrying the drug.

According to a first aspect of the present invention, there is provided a stent comprising a stent body of a cylindrical configuration having outer and inner surfaces, a first coated layer coating at least the outer surface of the stent body, and a second coated layer coating substantially completely over the first coated layer. The first coated layer is prepared of a first composition comprising a polymer and a vascular intimal hyperplasia inhibitor of a kind, which does not inhibit proliferation of endothelial cells, the weight compositional ratio of the polymer to the vascular intimal hyperplasia inhibitor being within the range of 8:2 to 3:7. On the other hand, the second coated layer is prepared of a polymer alone or a second composition comprising a polymer and a drug, the weight compositional ratio of the drug to 80% by weight of the polymer being less than 20% by weight.

In the practice of the present invention, the term "stent" referred to hereinabove and hereinafter is intended to mean a tubular medical instrument, which is, when a blood vessel or any other lumen within a living body is constricted or occluded, placed at the affected area of the blood vessel or lumen to expand the constricted or occluded site to secure a required lumen region. The stent of the kind referred to above has a diameter small enough for it to be inserted into the living body and is used to expand the constricted area to thereby increase the lumen diameter and then to maintain the affected area in an expanded state.

Also, in the practice of the present invention, the term "polymer" referred to hereinabove and hereinafter is used as a term intended to encompass a homopolymer, a copolymer and a mixture of polymers.

Each of the terms "first composition" and "second composition" referred to hereinabove and hereinafter as employed in the practice of the present invention is intended to mean a composition comprising a polymer and a drug, with the drug being dispersed in a polymer matrix (including either a dense structure or a porous structure) in the form of molecules or microdispersed solids. As will become clear from the description made hereinafter, in the first composition, the drug (argatroban) is preferably microdispersed in the polymer matrix whereas in the second composition, the polymer matrix is preferably a dense structure. The term "dense structure" referred to above and hereinafter is intended to mean a structure, in which no void is almost found when viewed through an optical microscope.

The vascular intimal hyperplasia inhibitor of a kind which does not inhibit the proliferation of the endothelial cells, employed in the practice of the present invention includes, for example, argatroban, ximelagatran, melagatran, dabigatran and dabigatran etexilate, but of them argatroban is preferably employed for the inhibitor. Accordingly, in the description of the present invention that follows, reference will be made to the use of argatroban as the vascular intimal hyperplasia inhibitor of the specific kind.

The argatroban employed in the practice of the present invention is a general term of (2R,4R)-4-methyl-1-[N$^2$-((RS)-3-methyl-1,2,3,4-tetrahydro-8-quinoline sulfonyl)-L-arginyl]-2-piperidine carboxylic acid hydrate that is expressed by the following chemical structural formula. It is to be noted that argatroban is well known in the art as a compound having an antithrombin effect. (See the Patent Documents 1 and 2 referred to hereinbefore.)

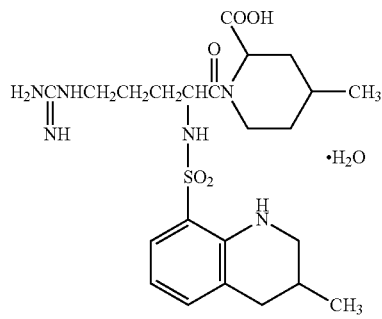

In a preferred embodiment of the first aspect of the present invention, the first coated layer preferably has a thickness within the range of 1 to 20 μm and the second coated layer preferably has a thickness within the range of 0.5 to 5 μm.

Argatroban employed in the first coated layer is preferably microdispersed in the polymer.

The first coated layer referred to above is preferably of a kind which does not contain any other drug than argatroban.

The second coated layer employed in the practice of the present invention is preferably prepared of the polymer alone.

Where the second coated layer is prepared of the second composition in the practice of the present invention, the drug contained in the second composition may be argatroban, rapamycin, everolimus, biolimus A9, zotarolimus, tacrolimus, paclitaxel or statin.

The polymer employed in the first composition and/or the second coated layer is preferably a biodegradable polymer.

In a preferred embodiment of the present invention, the biodegradable polymer referred to above may be a poly(lactic acid), poly(lactic acid-glycolic acid), poly(glycolic acid), poly(lactic acid-ε-caprolactone) or poly(glycolic acid-ε-caprolactone).

Also in the practice of the present invention, the stent body referred to above may be made of a metallic material, ceramic material or polymeric material. The stent body referred to above has a surface formed preferably with a diamond-like thin film.

According to a second aspect of the present invention, there is also provided a method of making a stent, in which the first composition referred to above is applied to at least an outer surface of the stent body with the use of a solution containing a mixed solvent, selected from the group consisting of a mixture of lower alkylketone and methanol, a mixture of lower alkyl ester and methanol or a mixture of lower halogenated hydrocarbon and methanol, followed by removal of the mixed solvent to thereby form the first coated layer.

Furthermore according to a third aspect of the present invention, there is provided a method of controlling the rate of release of argatroban from the stent, characterized in that the second coated layer in the stent, provided for according to the first aspect of the present invention discussed above, has a predetermined thickness so selected within the range of 0.5 to 5.0 μm that the respective rates of release of argatroban in a phosphate buffered saline at 37° C., which are measured on the first day and second day, respectively, subsequent to immersion of the stent in that phosphate buffered saline, are controlled to 3 μg/cm$^2$ per day or higher.

In a preferred embodiment of the present invention, the rate of release of argatroban in the phosphate buffered saline at 37° C., which is measured on the second day subsequent to immersion of the stent in that saline, may be controlled to 3 to 100 μg/cm$^2$ per day, by selecting the predetermined thickness of the second coated layer on the stent, provided for according to the first aspect of the present invention discussed above, so as to fall within the range of 0.5 to 5.0 μm.

Alternatively, the rate of release of argatroban in the phosphate buffered saline at 37° C., which is measured on the third to seventh day subsequent to immersion of the stent in that saline, may be controlled to 2 to 50 μg/cm$^2$ per day, by selecting the predetermined thickness of the second coated layer in the stent, provided for according to the first aspect of the present invention discussed above, so as to fall within the range of 0.5 to 5.0 μm.

The rate of release of argatroban contained in the first composition referred to above is preferably controlled by microdispersing the argatroban in the polymer.

Also, the rate of release of argatroban is preferably controlled by selecting the mixed solvent for dissolving the first composition from the group consisting of the mixture of a lower alkyl ester and methanol, the mixture of a lower alkyl ketone and methanol, and the mixture of a lower halogenated hydrocarbon and methanol, coating the surface of the stent body with the use of a solution, in which the first composition referred to above has been dissolved by the use of the selected solvent, and removing the mixed solvent, after the coating, to thereby form the first coated layer.

If the polymer used to form the second coated layer is lactic acid-glycolic acid-copolymer, the rate of release of argatroban is preferably controlled by changing the copolymerization ratio between the lactic acid and the glycolic acid.

Yet according to a fourth aspect of the present invention, there is provided a method of inhibiting vascular intimal hyperplasia, which includes placement of the stent of the structure according to the first aspect of the present invention within the blood vessel, allowing argatroban to be eluted from the indwelling stent to thereby suppress the vascular intimal hyperplasia without inhibiting the proliferation of the endothelial cells.

According to the first aspect of the present invention discussed hereinabove, since the vascular intimal hyperplasia inhibitor can be released persistently at a proper release rate due to the fact that the first coated layer contains the vascular intimal hyperplasia inhibitor (preferably argatroban) of a kind which does not inhibit proliferation of the endothelial cells, the weight compositional ratio of the polymer to the vascular intimal hyperplasia inhibitor being chosen to be within the range of 8:2 to 3:7 and that the first coated layer contains a substantial amount of the vascular intimal hyperplasia inhibitor and the second coated layer is prepared of the polymer alone or of a second composition comprising the polymer and the drug, the weight compositional ratio of the drug to 80% by weight of the polymer being chosen to be less than 20% by weight, the stent capable of exhibiting an effect of inhibiting the vascular intimal hyperplasia without inhibiting proliferation of the endothelial cells can be obtained. Considering that the second coated layer contains no drug and, if not, contains a slight amount of drug, particularly where the second coated layer contains no drug, the polymer matrix forming the second coated layer conserves the denseness, an effect of suppressing release of the drug (argatroban) contained in the first coated layer and allowing it to be released persistently is remarkable.

Also, the stent of the structure according to the first aspect of the present invention described hereinabove is preferably of a type in which the first coated layer has a thickness within the range of 1 to 20 μm and the second coated layer has a thickness within the range of 0.5 to 5 μm, the sum of the respective thickness of those first and second coated layers being less than 25 μm and preferably less than 20 μm, in order particularly to prevent the restenosis.

In the practice of the second aspect of the present invention described hereinabove, a lower alkylketone, lower alkyl ester and lower halogenated hydrocarbon that are used as a component of the mixed solvent for dissolving the first composition is a solvent for dissolving the polymer whereas methanol that is used as another component of the mixed solvent for dissolving the first composition is a solvent for dissolving the drug (argatroban). The use of this kind of one of those mixed solvents is effective to dissolve both of the polymer and the drug (argatroban), and since in the first coated layer prepared of the polymer and drug (argatroban) composition prepared by the use of this mixed solvent, the drug (argatroban) is not dissolved (molecular dispersed) in the polymer forming a component of the coated layer, but microdispersed, the control of the drug release rate can be characteristically easily accomplished by controlling the thickness of the second coated layer.

According to the third aspect of the present invention described hereinabove, in the stent of the construction according to the first aspect of the present invention, particularly by controlling the thickness of the second coated layer, which is formed on the first coated layer containing a high density of argatroban (preferably containing argatroban microdispersed in the polymer forming a component of the first coated layer), to a value within the range of 0.1 to 5 μm, the rate of release of argatroban can be controlled to a value falling within the above described range. In view of this, a desired drug release rate can be obtained.

Again according to the third aspect of the present invention, argatroban contained in the coated layer formed on the stent body can be released from the stent body at a rate of 3 μg/cm$^2$ per day or higher for at least two days subsequent to placement of the stent within the blood vessel, particularly the artery. In view of this, the argatroban so released can exhibit its inherent pharmacologic effect (suppression of vascular intimal hyperplasia) to thereby inhibit the occurrence of an in-stent restenosis. Also, in view of the fact that the whole intimal surfaces are covered by the endothelial cells one month the stent has been placed, such a meritorious effect can be obtained that thrombosis, particularly late thrombosis can be minimized as compared with the existing drug releasing stent.

The sustained drug-releasing stent according to the present invention can be effectively utilized in the practice of a stent treatment of the coronary artery, but can also be equally effectively utilized in the practice of a stent treatment of any other artery such as, for example, brain artery, renal artery and peripheral arteries.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims.

DESCRIPTION OF EMBODIMENTS

Stent Structure

Figure 1:
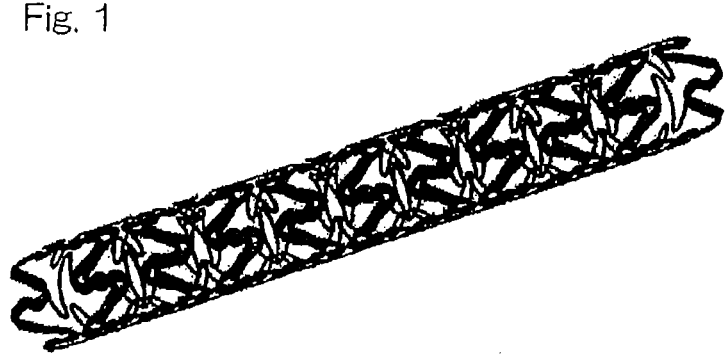
FIG. 1 is a perspective view showing one example of the shape of a stent body employed in the practice of the present invention.

Material that can be used to form a stent body is not specifically limited to a particular material, and any of those metallic, ceramic and polymer materials hitherto known in the pertinent art can be employed. However, of them, the metallic material having a high rigidity and a high corrosion resistance is preferred as a material for the stent body. Examples of such metallic material include stainless steel, tantalum, a nickel-titanium alloy (including nitinol), a magnesium alloy and a cobalt alloy (including an alloy containing cobalt, chromium and nickel). The stent body is of a structure having a cylindrical configuration and also having an outer surface and an inner surface opposite to the outer surface and may be a balloon expandable type, a self-expandable type or a combination thereof. FIG. 1 is a perspective view showing an example illustrating the shape of the stent body that is used in the practice of the present invention, particularly as a drug releasing stent. The mesh design of the stent body and the shape of struts are not specifically limited to particular ones, provided that a factor contributing to the in-stent restenosis, for example, a turbulent flow of blood in the vicinity of the inner wall of vessels and/or the mechanical stimulus brought by the projection of a bent portion of the struts to the blood vessel, so called a fish phenomenon, is below average. In any event, for the stent body utilized in the practice of the present invention, a stent body made of a cobalt alloy such as disclosed in the Japanese patents No. 3654627 and No. 3605388 may be employed, the disclosure of each of which is herein incorporated by reference as a part of this specification. Also, a stent body having a diamond-like thin film coated on a surface of the above described stent body to improve the biocompatibility thereof such as disclosed in the Japanese Patent No. 4066440 can also be used in the practice of the present invention and, accordingly, the disclosure of such Japanese patent is also herein incorporated by reference as a part of this specification. The stent body having a predetermined shape can be formed by means of a processing with the use of a laser processing machine or the like and subsequent surface finishing such as, for example, surface grinding or polishing.

(Coating over Stent Body)

In the practice of the present invention, at least an outer surface of a cylindrical surface of the stent body of the structure described above, preferably outer and inner surfaces thereof are formed with a polymer coated layer, in which a drug is carried to form a first coated layer. For a method of making the drug carried by the stent body surface, a dipping method in which the stent is immersed in a coating solution prepared by dissolving a drug and a polymer with the use of a suitable solvent, followed by removal from the coating solution to dry, a spray method in which a solution comprising the drug and the polymer dissolved therein with the use of the solvent is sprayed onto the stent, and a simultaneous spray method using two nozzles in which the drug and the polymer, which have been separately dissolved by the use of respective solvents, are sprayed simultaneously onto the stent can be enumerated and, although any of those methods can be employed in the practice of the present invention, a method, in which a coated layer of the polymer, in which the drug has been dispersed (or microdispersed), is formed on the stent body surface, is preferably employed since it is easy to control the drug release rate. In any event, it is preferred that in the first composition forming the first coated layer, the drug (argatroban) is microdispersed in the polymer.

(First and Second Coated Layers)

The basic structure of the stent utilized in the practice of the present invention comprises (a) a stent body, (b) a first coated layer formed on at least an outer surface of the stent body and comprising a polymer and a drug (preferably argatroban), (c) a second coated layer formed over the first coated layer and prepared of a polymer alone or of a mixture comprising a polymer and a drug and having the weight compositional ratio of the drug to 80% by weight of the polymer being less than 20% by weight. By allowing the first coated layer to carry a high concentration of the drug (argatroban) (in which the drug is retained in the polymer by means of molecular dispersion or microdispersion with particles in the nanometer or submicron order) and allowing the second coated layer to inhibit release of the drug (argatroban), the capability of sustained release of the drug for a prolonged period of time is imparted. By suitably selecting the thickness of the first coated layer, the state in which the drug (argatroban) is carried in the polymer in the first coated layer, the thickness of the second coated layer, and the polymer composition and structure in the second coated layer, the rate of release of the drug (argatroban) from the stent body surface can be controlled. For this reason, the second coated layer is required to be formed to substantially completely cover the first coated layer.

(First Composition for First Coated Layer)

The first coated layer is prepared of the first composition comprising the polymer and the drug (argatroban) as hereinabove described. The weight compositional ratio of the polymer to the drug (argatroban) in the first composition is within the range of 8:2 to 3:7 (the sum of the both being 10). If the proportion of the drug (argatroban) is less than 2, the rate of release of the drug (argatroban) from the coated layer is too low, but if it exceeds 7, the coated layer will become fragile, making it difficult to adhere to the stent base material. The first composition may contain, other than the polymer and the drug (argatroban), such a release auxiliary agent (carboxylic acid ester, monoester or diester of glycerin, preferably dimethyl tartrate or diethyl tartrate) as disclosed in the Patent Document 2 referred to hereinbefore. Due to the fact that in the first composition discussed above, the polymer carries the drug (argatroban) in a high concentration, the drug (argatroban) can be released persistently for a prolonged period of time. Accordingly, it is preferred that the first composition contain no other substance than the vascular intimal hyperplasia inhibitor (argatroban), so that it will not hamper for the polymer in the first composition to carry the drug (argatroban). Whether in the first composition the drug (argatroban) has been microdispersed in the polymer or whether it is molecular dispersed can be ascertained by determining the presence or absence of a thermal peak of crystal melting by means of a differential thermal analysis. (Microdispersion if the peak value is present and molecular dispersion if the peak value is absent.)

(Manner of Carrying Drug (Argatroban) in First Composition)

As hereinabove described, it is important for the drug (argatroban) to be released from the stent for a predetermined period of time subsequent to the placement of the stent in blood, particularly in the artery. With the stent according to the present invention, the rate of release of the drug (argatroban) is so controlled as to be equal to or higher than 3 $\mu g/cm^2$ in a phosphate buffered saline at 37° C., on the first day, and even on the second day, subsequent to immersion of the stent in that saline solution. In order for the rate of release of the drug (argatroban) to attain the above described value, it is preferred that the drug (argatroban) contained in the first composition is microdispersed (in the form of particles of the nanometer or submicron order) in the polymer as hereinbefore discussed, rather than being dissolved or molecular dispersed in the polymer. If the drug (argatroban) is dissolved in the polymer contained in the first composition, it will be difficult for a required amount of the drug to be released through the second coated layer within a predetermined time. In the first composition, while the drug (argatroban) is held in a carried state required to facilitate release thereof from the stent, suppressing the rate of release of the drug with the second coated layer so as to attain a predetermined value is effective for the control of the rate of release of the drug (argatroban).

(Polymer Comprising First Composition)

In the practice of the present invention, the focus is placed on the capability of releasing the drug (argatroban) in a quantity effective to suppress stenosis persistently for a predetermined period of time. For this purpose, in the first composition, the use of a flexible polymer of a kind having a glass transition temperature (Tg) within the range of −100 to 50° C., at which the drug (argatroban) can readily migrate within the polymer layer as a result of dispersion thereof, is preferred as a matrix polymer necessary for the drug (argatroban) to be carried. Examples of such a flexible polymer include silicone rubber, urethane rubber, fluorocarbon resin, poly(butyl acrylate) (−54° C.), poly(butyl methacrylate) (20° C.), acrylic rubber, natural rubber, an ethylene-vinyl acetate copolymer, a styrene-butadiene block copolymer, a styrene-isoprene block copolymer, and a styrene-isobutylene block copolymer. Although the flexible polymer of the kind referred to above is non-degradable when introduced into the blood vessel, in the practice of the present invention the use of a biodegradable polymer, particularly a biodegradable polymer of a kind capable of degrading in the living body to vanish within a period of half a year is preferred for coating where the blood vessel tissue is desired to be quickly recovered from chronic inflammation brought about by the polymer. Examples of the biodegradable polymer of the kind referred to above include poly(lactic acid), poly(lactic acid-glycolic acid), poly(glycolic acid), poly(lactic acid-ε-caprolactone), poly(glycolic acid-ε-caprolactone), poly-p-dioxananone, poly(glycolic acid-trimethylene carbonate), and poly-β-hydroxybutyric acid. Of them, the poly(lactic acid-glycolic acid), poly(lactic acid-ε-caprolactone) and poly(glycolic acid-ε-caprolactone) have a glass transition temperature within the range of −20 to 50° C. and has such a degrading rate as to degrade to vanish in the living body within a period of half a year and can therefore be preferably employed in the practice of the present invention. The molecular weight of any of those biodegradable polymers is preferred to be within the range of 20,000 to 500,000 in terms of securement of the strength of the coated layer and the working efficiency of coating.

(Selection of Polymer and Drug Release Rate)

The rate of release of the drug from the coated layer generally depends on the rate of diffusion of the drug in the polymer in the case of a non-biodegradable polymer, but it depends on the rate of diffusion of the drug and the rate of degradation of the polymer in the case of a biodegradable polymer. Accordingly, in order to control the drug release rate, the polymer should be properly selected and, if required, a combination of different polymers may be employed. Accordingly, by adjusting two parameters, that is, the rate of dispersion of the drug in the polymer and the rate of degradation of the polymer, the drug release rate can be controlled. In order to increase the rate of diffusion of the drug in the polymer, selection of a rubber-like polymer is appropriate, but in order to increase the biodegrading rate, selection of a copolymer containing a glycolic acid in a high copolymerization ratio is appropriate.

(Selection of Biodegradable Polymer and Drug Release Rate)

Where the biodegradable polymer is used as a polymer used in the preparation of the first composition, of those biodegradable polymers discussed above, the use of poly(lactic acid-glycolic acid) (copolymerization ratio=100:0 to 0:100) and poly(lactic acid-ε-caprolactone) (copolymerization ratio=100:0 to 25:75) is preferred in terms of the proven performance of successful use on human bodies and the proven absence of anything harmful to human bodies. The rate of degradation of the biodegradable polymer depends on the chemical structure of a monomer forming the polymer, the copolymerization ratio of the polymer and the molecular weight of the polymer and, accordingly, those parameters are preferred to be so adjusted as to suit to the intended drug release rate. In the case of the poly(lactic acid-glycolic acid), the degrading rate will increase if the proportion of glycolic acid is increased, and the copolymer having a molar ratio of 50:50 will degrade to vanish within the living body in about three months. Thus, if this kind of polymer is used, release of the drug will complete within a period of two months.

(Control of Drug Release Rate by Addition of Release Auxiliary Agent)

While the first composition referred to above comprises the polymer and the drug (argatroban) as hereinbefore described, an release auxiliary agent may be added to the first composition as a third component thereof, if required, to facilitate the rate of diffusion. The release auxiliary agent that can be suitably employed in the practice of the present invention includes dimethyl tartrate and diethyl tartrate such as disclosed in the Patent Document 2 referred to hereinbefore. Those release auxiliary agents may be employed either alone or in combination. As a preferred manner of adjusting the rate of release of the drug (argatroban), dimethyl tartrate and/or diethyl tartrate may be added to the biodegradable polymer coated layer. The amount of the release auxiliary agent(s) to be added may be suitably selected in consideration of the rate of release of the drug (argatroban), but it is preferably within about 5 to 60 phr of the weight of the polymer. If the amount is within this range, a favorable effect of addition can be obtained.

(Thickness of First Coated Layer)

The thickness of the coated layer of the stent per unit surface area (1 cm$^2$) is required to be within the range of 1 to 25 µm in order for the drug (argatroban) to be released in a proper quantity. Generally the range of 2 to 20 µm is preferred for that thickness. If the coated layer inclusive of the second coated layer exceeds 20 µm, there is a risk that the intra-stent constriction will become large and, therefore, the thickness of the first coated layer is preferred not to exceed 15 µm. Accordingly, in order to satisfy those coating condition described above, the composition of the coating solution and the coating condition are suitably selected. The first coated layer may be comprised of a single layer or a plurality of layers provided that the total thickness falls within the above discussed range.

(Second Composition)

The second coated layer may be prepared of the polymer alone, but as a component other than the polymer, such a drug as, for example, an antithrombotic drug (argatroban or the like), an immunosuppressor (rapamycin, everolimus, biolimus A9, zotarolimus, tacrolimus or the like), an anticancer drug (paclitaxel or the like) and/or a hypocholesterolemic agent (statin or the like) may be mixed with the polymer in a quantity that is less than 20 wt % relative to 80 wt % of the polymer. Also, such a component as a biological component such as, for example, protein, inorganic or organic salts, amino acids, polysaccharides, sugars, and a release auxiliary agent such as, for example, dimethyl tartrate and diethyl tartrate contributes to the control of the rate of penetration of the drug (argatroban) from the first coated layer to the second coated layer (top coat layer) and may, depending on the circumstances, contribute to suppression of platelet aggregation, suppression of thrombus formation, suppression of proliferation of smooth muscle and/or curing of endothelium and, therefore, it may be added in a suitable quantity not exceeding 20 wt %.

(Polymer Forming Second Coated Layer)

In the practice of the present invention, the second coated layer (top coat layer) prepared of the polymer alone or the second composition is coated over the first coated layer (base coat layer) prepared of the first composition so that the rate of release of the drug from the first coated layer can be suppressed with a sustained release capability imparted thereto. A material capable of migrating within the top coat layer at an appropriate rate due to the diffusion of the drug (argatroban) is preferably used as a component forming the second composition referred to above. The material satisfying this condition can be suitably employed in the form of a flexible polymer having a molecular weight within the range of 10,000 to 500,000 and also having a glass transition temperature within the range of −100 to 60° C. Examples of the polymer of that kind include non-biodegradable polymers such as, for example, silicone rubber, urethane rubber, fluorocarbon resin, poly(butyl acrylate) (−54° C.), poly(butyl methacrylate) (20° C.), acrylic rubber, natural rubber, an ethylene-vinyl acetate copolymer, a styrene-butadiene block copolymer, a styrene-isoprene block copolymer, a styrene-isobutylene block copolymer. Where the blood vessel tissue is desired to be quickly recovered from chronic inflammation brought about by the polymer, the use of the biodegradable polymer is preferred and the use of the biodegradable polymer of a kind capable of degrading in the living body to vanish within a period of half a year is more preferred. Examples of the biodegradable polymer of the kind referred to above and which can be employed in the practice of the present invention include a poly(lactic acid), poly(lactic acid-glycolic acid), poly(glycolic acid), poly(lactic acid-ε-caprolactone), poly(glycolic acid-ε-caprolactone), poly-p-dioxananone, poly(glycolic acid-trimethylene carbonate), and poly-(β-hydroxybutyric acid), but of them, the poly(lactic acid-glycolic acid) and poly(lactic acid-ε-caprolactone), poly(glycolic acid-ε-caprolactone) are preferably employed since they have a glass transition temperature within the range of −20 to 60° C. and has such a degrading rate as to degrade to vanish in the living body within a period of half a year. The molecular weight of any of those biodegradable polymers is preferred to be within the range of 10,000 to 500,000 in terms of securement of the strength of the coated layer and the working efficiency of coating. The polymer used in the second coated layer may be the same as or different from the polymer used in the first coated layer and vice versa.

(Thickness of the Second Coated Layer)

The second coated layer has a film thickness preferably within the range of 0.5 to 5 μm. If it is less than the lower limit of 0.5 μm, no film uniformity of the second coated layer can be obtained to such an extent that the rate of release of the drug (argatroban) can no longer be controlled. Conversely, if it exceeds the upper limit of 5 μm, there is a risk that the drug (argatroban) release rate will become too low. The second coated layer may be a single layer alone, but may be comprised of a plurality of layers so long as the requirement of the thickness thereof satisfies the above discussed thickness range.

(Method of Forming First Coated Layer)

In order to coat the stent body surface with the matrix polymer carrying the drug (argatroban), either is a coating solution prepared by dissolving the drug and the polymer in an easily volatilizable solvent (for example, fluorinated alcohol), sprayed onto the stent body surface, or the stent body is immersed in such coating solution, to thereby apply the coating solution to the stent body, followed by drying the stent body to form the intended first coated layer. In the practice of the present invention, the first composition containing the drug (argatroban) is coated on at least the outer surface (the surface of the stent body which may contact the wall of the blood vessel) of the stent body of the cylindrical configuration. In such case, the coating solution containing the first composition dissolved in the solvent is preferably applied to the outer surface of the stent body by means of a spraying technique. Also, where not only the outer surface of the stent body, but also the inner surface thereof is desired to be coated, the solution so prepared may be sprayed onto both of those stent body surfaces. Alternatively, application of such coating solution to the stent body surfaces may be accomplished by dipping the stent body into the solution. Removal of the solvent after the coating may be suitably accomplished by means of depressurization, air blasting or heating.

(Surface Treatment of Stent Body)

When the coating solution so prepared in the manner described above is applied to the stent body surface, it is necessary for the coated layer, left after volatilization of the solvent, to adhere to the stent body surface, and, therefore, prior to the coating taking place, the stent body surface has, if required or necessary, to be cleansed or surface activated. The surface treatment for this purpose may be one or a combination of chemical treatment utilizing an oxidizing reagent or fluorine gas, surface graft polymerization, plasma discharge treatment, corona discharge treatment, UV/ozone treatment and electron irradiation.

(Selection of Solvent for Preparation of First Composition)

As a volatile solvent having a boiling point lower than 100° C. and capable of dissolving the drug (argatroban) and readily removable from the stent body after coating, methanol, ethanol, trifluoroethanol, hexafluoroisopropanol and a mixed solvent comprising the above mentioned alcohol(s) can be enumerated. Although for the polymer any of those polymers as enumerated hereinbefore can be employed, the use of either of poly(lactic acid-glycolic acid) or poly(glycolic acid-ε-caprolactone) having a high polarity is desirable in terms of solubility to the above described coating solution. As a solvent capable of solving both of the drug (argatroban) and any of those polymers referred to above and, also, capable of providing a sustained release capability of the drug, other than trifluoroethanol and hexafluoroisopropanol referred to above, a mixture of one of lower alkyl esters (having the carbon number not greater than 6) such as, for example, ethyl acetate, methyl acetate, butyl acetate with methanol, a mixture of one of lower alkyl ketones (having the carbon number not greater than 6) such as, for example, acetone and methyl ethyl ketone with methanol, and a mixture of one of lower halogenated hydrocarbons (having the carbon number not greater than 4) such as, for example, methylene chloride, chloroform and dichloroethane with methanol can be enumerated. Of those mixed solvents, the use of one of the mixed solvent containing the lower alkyl ester and methanol, the mixed solvent containing the lower alkyl ketone and methanol, and the mixed solvent containing the lower halogenated hydrocarbon and methanol is desirable in terms of the availability of the sustained release capability of the drug. Where the solvent is removed from the coated layer having been prepared by the use of any of those mixed solvents enumerated above due to the drug (argatroban) being microdispersed in the polymer, the drug (argatroban) is carried having been microdispersed in the polymer and, when the second coated layer is formed thereover, the desirable rate of release of the drug (argatroban) is achieved.

(Formation of Second Coated Layer)

The second coated layer is formed by applying a solution comprising the polymer dissolved in the solvent, or a solution containing the second composition comprising the polymer and other components, over the first coated layer. The coating method that can be employed to form the second coated layer is similar to that used to form the first coated layer.

(Formation of Second Composition)

As a solvent used to form the polymer necessary to form the second coated layer or the second composition comprising the polymer and the other component, the solvent used to form the previously described first composition can be employed, but the method of coating by the use of a solvent of a kind, which does not dissolve argatroban, but dissolves the polymer and the other component (such as lower alkyl ester, lower alkyl ketone or lower halogenated hydrocarbon) is preferably used since it can precisely control the rate of release of the drug. In such case, the second composition does not contain argatroban.

(Control of Drug Release Rate)

In order for the sustained drug-releasing stent according to the present invention to markedly suppress the in-stent restenosis, as is clear from results of experiments conducted on animals as disclosed in Examples below, the inventors of the present invention have found that it is necessary to control such a drug release rate that for at least two days subsequent to immersion of the stent in a phosphate buffered saline of 7.4 in pH value and at 37° C., argatroban can be released at a rate of 3 μg/cm$^2$ per day or higher, preferably 4 μg/cm$^2$ per day or higher and more preferably 6 μg/cm$^2$ per day or higher. Also, though the upper limit of the drug release rate is not specifically determined in consideration of the restenosis prevention effects, the use of the drug in a too much amount will result in side effects such as bleeding and, also, the use of the drug in an amount greater than necessary is undesirable in terms of the manufacturing cost and, therefore, it appears proper to choose 500 μg/cm$^2$ per day, or generally 300 μg/cm$^2$ per day, for the highest drug release rate. It is to be noted that the drug release rate for the third day and thereafter will not be considered as an essential condition for the suppression of the in-stent restenosis, but since it is expected that the persistent release of argatroban on the third day and thereafter will enhance the restenosis prevention effects, it is preferred that the drug release rate of equal to or higher than 2 μg/cm$^2$ per day can be sustained for 1 to 2 weeks subsequent to the third day of use following the intravascular placement of the stent. As the method for releasing argatroban at a rate of 3 μg/cm$^2$ per day or higher for at least first two days subsequent to the intravascular placement of the stent, the drug coated layer according to the present invention is particularly preferred. In other words, with the stent comprising the first composition, comprising 20 to 70 wt % of argatroban and 80 to 30 wt % of polymer and uniformly coated on at least the outer surface of the cylindrical stent body to provide the first coated layer having a thickness within the range of 1 to 15 μm and, at the same time, the polymer or the second composition, comprising the polymer and the drug in a quantity less than 20 wt % relative to 80 wt % of the polymer and uniformly coated over the first coated layer so as to substantially completely cover the outer surface of the first coated layer to thereby provide the second coated layer, control of the argatroban release rate to 3 μg/cm$^2$ per day or higher, preferably 4 μg/cm$^2$ per day or higher and more preferably 6 μg/cm$^2$ per day or higher at least two days subsequent to the immersion of the stent in the phosphate buffered saline of 7.4 in pH value at 37° C. can be accomplished.

Owing to the fact that the drug (argatroban) is carried by the polymer of the first composition in a high concentration and that the second coated layer is prepared of the polymer alone or even though the layer containing the drug, since it is formed of the composition containing the drug in a small content, that is, less than 20 wt %, and therefore it has a dense polymer layer with the thickness within the range of 0.5 to 5.0 μm, the drug (argatroban) release rate is suppressed, resulting in achieving a sustained release. In particular, in the first coated layer, the drug (argatroban) is preferably carried by the polymer as microdispersed therein. In order for the drug (argatroban) to be carried in the form as microdispersed, it can be accomplished by suitably selecting a solvent that is used to adjust the composition comprising the polymer and the drug (argatroban) as hereinbefore described.

The drug (argatroban) release rate is affected by the polymers contained in the first composition and forming the second coated layer, but can be controlled by changing the thickness of the coated layer within the previously described range with the polymer employed. Of the polymers, a copolymer of lactic acid and glycolic acid is preferably employed.

EXAMPLES

Hereinafter, the present invention will be specifically demonstrated by way of examples, which are described only for the purpose of illustration and are not intended to limit the scope of the present invention. Materials, numerical values of, for example, the amounts of use, the concentrations and processing temperatures, and processing methods, which are employed and set forth in the following examples are of course only for the purpose of illustration and should not be construed as limiting the scope of the present invention.

Preparing Example 1

A uniformly mixed solution (coating solution) was prepared by dissolving 140 mg of argatroban and 160 mg of D,L-lactic acid/glycolic acid copolymer (mole ratio: 50/50) uniformly with the use of 20 mL of 2,2,2-trifluoroethanol. A stent body (hereinafter referred to as Stent 1) of such a design as shown in FIG. 1 and having the total surface are of 0.70 cm$^2$, a length of 17 mm, an inner diameter of 3 mmφ when dilated and an outer diameter of 1.55 mmφ when processed, was mounted on a mandrel of a spray type coating apparatus. The coating solution so prepared was sprayed from a nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. 30 stent bodies were coated in the manner described above under the same conditions. When those stent bodies were measured to the unit of μg by means of a microbalance, it has been found that an average quantity of 619 μg of the mixture containing argatroban and the copolymer referred to above was coated on those stent bodies. (Average thickness of the first coated layer: 7.4 μm) Those stent bodies are hereinafter referred to as DES 1.

Preparing Example 2

A uniformly mixed solution (coating solution) was prepared by dissolving 300 mg of D,L-lactic acid/glycolic acid copolymer (mole ratio: 50/50) uniformly in 20 mL of chloroform. The DES 1 prepared in Preparing Example 1 described above was mounted on a mandrel of a spray type coating apparatus. The coating solution so prepared was sprayed from a nozzle at a rate of 20 μL/min. and the stent body, held 9 mm below the nozzle and rotated at a rate of 120 rpm together with the mandrel, was reciprocatingly moved to allow the sprayed solution to be applied for about 100 seconds to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. Under the same conditions, 15 stent bodies were coated in the manner described above. When those stent bodies were measured by means of a microbalance, it has been found that the copolymer referred to above was coated in a quantity of 103 µg on average. (Average thickness of the second coated layer: 1.2 µm) Hereinafter, the stent bodies formed with those two layers (Coating Total Amount: 722 µg, and Average Coated Layer Thickness: 8.6 µm) are hereinafter referred to as DES 2.

Preparing Example 3

A uniformly mixed solution (coating solution) was prepared by dissolving 120 mg of argatroban and 180 mg of D,L-lactic acid/glycolic acid copolymer (mole ratio: 50/50) uniformly with the use of 20 mL of 2,2,2-trifluoroethanol. The Stent 1 referred to previously was mounted on a mandrel of a spray type coating apparatus. The coating solution so prepared was sprayed from a nozzle at a rate of 20 µL/min. and the Stent 1, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. 30 stent bodies were coated in the manner described above under the same conditions. When those stent bodies were measured to the unit of µg by means of a microbalance, it has been found that an average quantity of 493 µg of the mixture containing argatroban and the copolymer referred to above was coated on those stent bodies. (Average thickness of the first coated layer: 5.9 µm) Those stent bodies are hereinafter referred to as DES 3.

Preparing Example 4

A uniformly mixed solution (coating solution) was prepared by dissolving 300 mg of D,L-lactic acid/glycolic acid copolymer (mole ratio: 50/50) uniformly in 20 mL of chloroform. The DES 3 was mounted on a mandrel of a spray type coating apparatus. The coating solution so prepared was sprayed from a nozzle at a rate of 20 µL/min. and the stent body, held 9 mm below the nozzle and rotated at a rate of 120 rpm together with the mandrel, was reciprocatingly moved to allow the sprayed solution to be applied for about 100 seconds to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. Under the same conditions, 15 stent bodies were coated in the manner described above. When those stent bodies were measured by means of a microbalance, it has been found that the copolymer referred to above was coated in a quantity of 148 µg on average. (Average thickness of the second coated layer: 1.8 µm) Hereinafter, the stent bodies formed with those two layers (Coating Total Amount: 641 µg, and Average Coated Layer Thickness: 7.6 µm) are hereinafter referred to as DES 4.

Preparing Example 5

A uniformly mixed solution (coating solution) was prepared by dissolving 120 mg of argatroban and 180 mg of D,L-lactic acid/glycolic acid copolymer (mole ratio: 50/50) uniformly with the use of 20 mL of an acetone/methanol mixed solvent (Volume ratio: 7:3). The Stent 1 referred to previously was mounted on a mandrel of a spray type coating apparatus. The coating solution so prepared was sprayed from a nozzle at a rate of 20 µL/min. and the Stent 1, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. 30 stent bodies were coated in the manner described above under the same conditions. When those stent bodies were measured to the unit of µg by means of a microbalance, it has been found that an average quantity of 583 µg of the mixture containing argatroban and the copolymer referred to above was coated on those stent bodies. (Average thickness of the first coated layer: 6.9 µm) Those stent bodies are hereinafter referred to as DES 5.

Preparing Example 6

A uniformly mixed solution (coating solution) was prepared by dissolving 300 mg of D,L-lactic acid/glycolic acid copolymer (mole ratio: 50/50) uniformly in 20 mL of ethyl acetate. The DES 5 was mounted on a mandrel of a spray type coating apparatus. The coating solution so prepared was sprayed from a nozzle at a rate of 20 µL/min. and the stent body, held 9 mm below the nozzle and rotated at a rate of 120 rpm together with the mandrel, was reciprocatingly moved to allow the sprayed solution to be applied for about 100 seconds to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. Under the same conditions, 15 stent bodies were coated in the manner described above. When those stent bodies were measured by means of a microbalance to the unit of µg, it has been found that the copolymer referred to above was coated in a quantity of 255 µg on average. (Average thickness of the second coated layer: 3.0 µm) Hereinafter, the stent bodies formed with those two layers (Coating Total Amount: 838 µg, and Average Coated Layer Thickness: 10.0 µm) are hereinafter referred to as DES 6.

Preparing Example 7

A uniformly mixed solution (coating solution) was prepared by dissolving 300 mg of D,L-lactic acid/glycolic acid copolymer (mole ratio: 50/50) uniformly in 20 mL of 2,2,2-trifluoroethanol. The Stent 1 was mounted on a mandrel of a spray type coating apparatus. The coating solution so prepared was sprayed from a nozzle at a rate of 20 µL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. Under the same conditions, 10 stent bodies were coated in the manner described above. When those stent bodies were measured by means of a microbalance to the unit of µg, it has been found that the copolymer referred to above was coated in a quantity of 487 µg on average. (Average thickness of the coated layer: 5.8 µm) Hereinafter, the stent bodies so formed are hereinafter referred to as PCS 1.

<Drug Release Test 1>

The drug release rate of each of six types of the drug coated stents prepared respectively as described in Preparing Examples 1 to 6 was measured. For this purpose, each of those drug coated stents was mounted on a balloon catheter of 3 mm in diameter and 20 mm in length and was then sterilized with an ethylene oxide gas (EOG). After the sterilization, the balloon catheter carrying the respective drug coated stent was inflated at about 12 atmosphere for 30 seconds to expand to a diameter of 3 mm. The three drug coated stents were placed within sealed clean glass containers and 30 mL of a phosphate buffered saline having a pH value of 7.4 was added to each of those glass containers. In a condition in which those stents were completely immersed in the solutions, those containers were shaken within a temperature controlled oven at 37° C.

The UV absorption (331 nm) of the elute obtained at intervals of a predetermined time was measured using a commercially available ultraviolet visible spectrometer, UV-2450 manufactured by and available from Shimadzu Corporation to determine the absorbance exhibited by argatroban. An analytical curve was prepared using phosphate buffered salines containing argatroban in a concentration of 0.001% or 0.0001%, and the absorbance was converted into concentration to determine the released quantity of argatroban per 1 cm² of the stent surface area. Results are tabulated in Table 1 below.

TABLE 1

Drug Release Rates exhibited by DES 1 to 6.

| Stents | Drug release rate after 0 to 24 hours of immersion (µg/cm² per day) | Drug release rate after 24 to 48 hours of immersion (µg/cm² per day) | Drug release rate after 48 to 72 hours of immersion (µg/cm² per day) | Drug release rate after 72 to 96 hours of immersion (µg/cm² per day) |
|---|---|---|---|---|
| DES 1 | 374 | 1 | 0 | 0 |
| DES 2 | 153 | 6 | 4 | 3 |
| DES 3 | 131 | 0 | 0 | 0 |
| DES 4 | 77 | 4 | 2 | 2 |
| DES 5 | 301 | 0 | 0 | 0 |
| DES 6 | 241 | 21 | 6 | 1 |

Table 1 above makes it clear that no burst-like abrupt release of the drug within 24 hours subsequent to the immersion into the phosphate buffered saline was found in each of the drug coated stents (DES 2, DES 4 and DES 6) each having the two coated layers and that the released quantity of argatroban within 24 to 48 hours subsequent to the immersion into the phosphate buffered saline was 4 µg/cm² or higher, having exhibited a sufficient release of the argatroban.

<Animal Test 1>

Six types of six stents including the drug releasing stents (DES 1, DES 2, DES 4 and DES 6) prepared by the respective methods described in Preparing Examples 1, 2, 4 and 6 above, the stents (PCS 1) described in Preparing Example 7 and coated with only the polymer layer, and the Stent 1, totaling 36 stents, were implanted in coronary arteries (LAD, LCX) of 18 heads of Clawn miniature pigs (weighing 25 to 40 kg) and, one month thereafter, the in-stent restenosis occurring in each of those miniature pigs was evaluated according to the quantitative coronary angiography (QCA).

Each of those stents was mounted on a balloon catheter and was subsequently sterilized with EOG. While each of the miniature pig was held under general anesthesia, the respective stent was inserted from the right pig femoral artery into the pig coronary artery through a 6 Fr guiding catheter, using a sheath introducer. The stent so inserted was dilated by selecting the site of implantation and the stent expanding pressure so that the diameter (proximal site) of coronary artery after implantation of the stent can attain a value within the range of 1.0 to 1.2 relative to the initial diameter of the coronary artery, followed by implantation of the stent. During a period of 33 days starting from three days prior to the implantation and terminating when the stent was removed, 100 mg of aspirin and 50 mg of clopidogrel, mixed in a feed, were administrated together with the feed.

Thirty days after the implantation, lumen diameters of the implanted stent at respective locations proximal, medial and distal were determined by contrast radiography. The percent diameter stenosis is calculated according to the following equation.

Percent Diameter Stenosis=[(lumen diameter immediately after implantation)−(lumen diameter one month after implantation)]/(lumen diameter immediately after implantation)×100

The average percent diameter stenosis so calculated is tabulated in Table 2 below.

TABLE 2

Relation Between Drug Release Amount and Rate of Diameter Restenosis 30-days After Implantation

| Stents Indwelled in Mini. Pigs | Examples & Comparisons | Amt. of Drug released during 24 to 48 hours (µg/cm² per day) | Average Percent Diameter Stenosis (%) (N = 6) |
|---|---|---|---|
| DES 1 | Comp. 1 | 1 | 65 |
| DES 2 | Example 1 | 6 | 29 |
| DES 4 | Example 2 | 4 | 36 |
| DES 6 | Example 3 | 21 | 27 |
| PCS 1 | Comp. 2 | 0 | 62 |
| Stent 1 | Comp. 3 | — | 41 |

As can readily be understood from Table 2 above, the DES 4 (Example 2), which exhibited the drug release rate of 4 µg/cm² per day or higher during the period of 24 to 48 hours, has also exhibited a lower diameter stenosis than that exhibited by the Stent 1 (Comparison 3). In contrast thereto, the DES 1 (Comparison 1), which showed the drug release rate of 1 µg/cm² or lower per day, has showed a diameter stenosis substantially equal to that exhibited by the PCS 1 (Comparison 2), which did not contain any drug, and has also showed no effect of preventing the stenosis. Yet, the DES 1 (Comparison 1) referred to above has showed a greater diameter stenosis than that exhibited by the Stent 1 (Comparison 3), which has no coating, and showed an adverse effect brought about by the polymer coating.

<Animal Test 2>

Figure 2:
FIG. 2 is a diagram of a pathological sample showing a section of a blood vessel of DES2.
Figure 3:
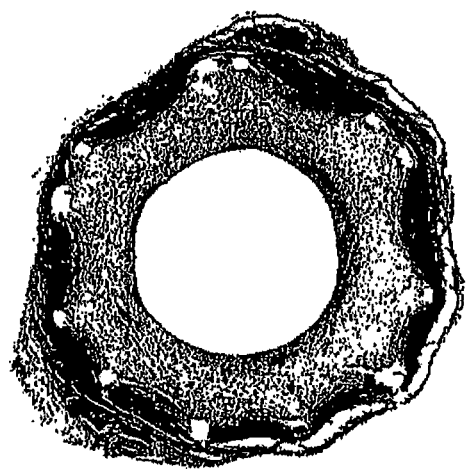
FIG. 3 is a diagram of a pathological sample showing a section of a blood vessel of DES5.

The six stents (DES 2), prepared by the methods described in Preparing Example 2 above, and the six stents (DES 5) (Comparison 4), prepared by the methods described in Preparing Example 5 above, were implanted in 12 coronary arteries (LAD, LCX) of 6 heads of Clawn miniature pigs (weighing 25 to 36 kg) in accordance with the procedures employed in the Animal Test 1 discussed above and, 28 days thereafter, those pigs were dissected to remove hearts which were fixed in formalin. Thereafter, stented vessels were dissected from the hearts. After fixation of them with acrylic resin, the test pieces were prepared by cutting out of the fixed tissues at three locations, corresponding to both of distal ends and intermediate portion of the respective stents, to provide a test piece of 6 μm in thickness. Those test pieces were subsequently stained according to the hematoxylin eosin staining method and the Elastica-van Gieson method, followed by evaluation to determine the area stenosis (%) and the rate of endothelialization (%). The area stenosis with the DES 2 was found to be 28±8%, which was substantially in consistency with the average percent diameter stenosis exhibited in Example 1. The rate of endothelialization exhibited by the DES 2 was found to be 100%, showing that injuries to the inner wall of blood vessels, which occurred at the time of placement of the stents, were completely repaired. The area stenosis with the DES 5 was found to be 64±16%, which was substantially in consistency with the average percent diameter stenosis exhibited in Comparisons 1 and 2. For the purpose of comparison, an example of the histopathological samples of the DES 2 is shown in FIG. 2 and that of the DES 5 is shown in FIG. 3.

Thus, the coronary stent having a capability of accomplishing a sustained release of the drug could have been prepared, which is so designed and so configured that argatroban carried on the surface of the coronary stent can be released from such stent at a rate of between 3 to 300 μg/cm² per day in the phosphate buffered saline at 37° C. and having a pH value of 7.4, for at least two days subsequent to immersion of the stent in such saline solution. The drug elusion tests and the animal tests, which have been discussed hereinbefore, are believed to have proven that when this coronary stent is implanted in the coronary artery, the argatroban so released therefrom could effectively inhibit the vascular intimal hyperplasia and, within one month after stenting, the inner wall of vessels could be completely covered by the endothelial cells.

Preparing Example 8

A uniformly mixed solution (coating solution) was prepared by dissolving 140 mg of argatroban and 160 mg of poly(D,L-lactic acid-glycolic acid) (mole ratio: 65/35) uniformly with the use of 20 mL of a mixed solvent containing acetone and methanol mixed in a volume ratio of 7:3. After a stent body made of a cobalt alloy and coated with a diamond-like thin film, which stent is of a shape similar to the previously referred to Stent 1, had been subjected to the plasma discharge treatment, the stent body was mounted on a mandrel of a spray coating apparatus. The coating solution so prepared was sprayed from a nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. 10 stent bodies were coated in the manner described above under the same conditions. When those stent bodies were measured to the unit of μg with the use of a microbalance, it has been found that an average quantity of 643 μg of the mixture containing argatroban and the copolymer referred to above was coated on those stent bodies. (Average thickness of the first coated layer: 7.7 μm) Those stent bodies are hereinafter referred to as DES 7.

Preparing Example 9

A uniformly mixed solution (coating solution) was prepared by dissolving 150 mg of poly(D,L-lactic acid-glycolic acid) (mole ratio: 65/35) uniformly in 20 mL of the mixed solvent containing acetone and methanol. The DES 7 prepared in Preparing Example 8 described above was mounted on a mandrel of a spray type coating apparatus. The coating solution so prepared was sprayed from a nozzle at a rate of 20 μL/min. and the stent body, held 9 mm below the nozzle and rotated at a rate of 120 rpm together with the mandrel, was reciprocatingly moved to allow the sprayed solution to be applied for about 180 seconds to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature controlled vacuum drying oven to remove the solvent completely. Under the same conditions, 10 stent bodies were coated in the manner described above. When those stent bodies were measured with the use of a microbalance, it has been found that the copolymer referred to above was coated in a quantity of 241 μg on average was coated on those 10 stent bodies. (Average thickness: 2.9 μm) Hereinafter, the stent bodies formed with those two layers (Coating Total Amount: 884 μg, and Average Coated Layer Thickness: 10.5 μm) are hereinafter referred to as DES 8.

Example 4

<Drug Release Test 2>

The rate of release of the drug from the drug coated stents referred to the Preparing Example 8 above, was measured. For this purpose, each of those drug coated stents was mounted on a balloon catheter of 3 mm in diameter and 20 mm in length and was then sterilized with an ethylene oxide gas (EOG). After the sterilization, the balloon catheter carrying the respective drug coated stent was inflated at about 12 atmosphere for 30 seconds to expand to a diameter of 3 mm. The three drug coated stents were placed within sealed clean glass containers and 30 mL of a phosphate buffered saline having a pH value of 7.4 was added to each of those glass containers. In a condition with those stents completely immersed in the solutions, those containers were shaken within a temperature controlled oven at 37° C.

The UV absorption (331 nm) of the elute obtained at intervals of a predetermined time was measured using a commercially available ultraviolet visible spectrometer, UV-2450 manufactured by and available from Shimadzu Corporation to determine the absorbance exhibited by argatroban. An analytical curve was prepared using phosphate buffered salines containing argatroban in a concentration of 0.001% or 0.0001%, and the absorbance was converted into concentration to determine the released quantity of argatroban per 1 cm$^2$ of the stent surface area. Results are tabulated in the following table below.

TABLE 3

Drug Release Rate exhibited by DES 8

| Stents | Drug release rate after 0 to 24 hours of immersion (μg/cm$^2$ per day) | Drug release rate after 24 to 48 hours of immersion (μg/cm$^2$ per day) | Drug release rate after 48 to 72 hours of immersion (μg/cm$^2$ per day) | Drug release rate after 72 to 96 hours of immersion (μg/cm$^2$ per day) |
|---|---|---|---|---|
| DES 8 | 165 | 54 | 24 | 13 |

Table 3 above makes it clear that no burst-like abrupt release of the drug within 24 hours subsequent to the immersion into the phosphate buffered saline was found in the drug coated stent DES 8 having the two coated layers and that the released quantity of argatroban within 24 to 48 hours subsequent to the immersion into the phosphate buffered saline was 46 μg/cm$^2$ or higher, having exhibited a sufficient release of the argatroban.

Examples 5 to 8

30 mg of argatroban and 90 mg of poly(D,L-lactic acid-glycolic acid) (mole ratio: 65/35) were dissolved in 5 mL of each of four different solvents, listed in Table 4 below, and the resultant mixtures were cast on a glass plate. After the cast films on the glass plate had been dried at room temperature for 6 hours, they were dried at 60° C. for 17 hours within a vacuum drying oven, followed by recovery of polymer coated films containing argatroban from the glass plate. Each of the resultant cast films was thermally analyzed using a DSC apparatus (differential scanning calorimeter). With the temperature increased at a rate of 5° C. per minute from the room temperature to 210° C., the crystal melting temperature of argatroban (endothermic peak temperature) was measured. The result of measurement for each of the cast films are shown in Table 4. The coating (cast film) prepared with the use of 2,2,2-trifluoroethanol showed no endothermic peak during the temperature increase from the room temperature to 210° C. and, accordingly, it could be surmised that argatroban had been molecular dispersed in the polymer. On the other hand, in the case where the mixed solvent containing acetone and methanol, the mixed solvent containing ethyl acetate and methanol and the mixed solvent containing 1,2, dichloroethane and methanol were employed, the endothermic peak resulting from crystalline melting of argatroban appeared at a temperature of about 178° C. In view of these, it has been ascertained argatroban captured into the polymer are dispersed in different manners depending on the kind of solvent used.

Each of the cast films referred to above was then cut to a film piece having a surface area of 3 cm$^2$ and 30 mL of a phosphate buffered saline having a pH value of 7.4 was added. With the stent completely immersed in the saline solution, the saline solution was shaken within a temperature controlled oven at 37° C. The UV absorption (331 nm) of the elute obtained on the second to seventh days subsequent to the start of immersion in the saline solution was measured using a commercially available ultraviolet visible spectrometer, UV-2450 manufactured by and available from Shimadzu Corporation to determine the absorbance exhibited by argatroban. An analytical curve was prepared using phosphate buffered salines containing argatroban in a concentration of 0.001% or 0.0001% and the absorbance was converted into concentration to determine the amount of argatroban released per 1 cm$^2$ of the stent surface area. Results are tabulated in Table 4 below. The released quantity of argatroban in each of Examples 5, 6 and 7 is found to be of a value higher ten times that exhibited in Example 5, in which no endothermic peak appeared.

TABLE 4

Endothermic Characteristic of Drug Coated Layers in Films Prepared with the Use of Different Solvents

| | Solvents Used | Endothermic Peak (° C.) | Release Amt. (μg/cm$^2$ per day) |
|---|---|---|---|
| Example 5 | 2,2,2-trifluoroethanol | None | 8 |
| Example 6 | Acetone and Methanol Mixed Solvent (Vol. Ratio = 7:3) | 178 | 101 |
| Example 7 | Ethyl Acetate and Methanol Mixed Solvent (7:3) | 178 | 87 |
| Example 8 | 1,2-dichloroethane and Methanol Mixed Solvent (7:3) | 178 | 83 |

<Animal Test 3>

10 stents (DES 8), prepared in Preparing Example 8 and 10 commercially available drug releasing stents (trade-named "Cyper" manufactured by and available from Johnson and Johnson), in which rapamycin (immunosuppressor) is used as a vascular intimal hyperplasia inhibitor, were implanted in coronary arteries (LAD, LCX and RCA) of 8 heads of Clawn miniature pigs (weighing 27 to 43 kg) according to the procedures set forth under the Animal Test 1 above and, 90 days thereafter, those pigs were dissected to remove hearts which were subsequently fixed in formalin. Thereafter, stented vessels were dissected from the hearts. After fixation of them with acrylic resin, the test pieces were prepared by cutting out of the fixed tissues at three locations, corresponding to both of distal ends and intermediate portion of the respective stents, to provide a test piece of 6 μm in thickness. Those test pieces were subsequently stained according to the hematoxylin eosin staining method and the Elastica-van Gieson method, followed by evaluation to determine the area stenosis (%) and the rate of endothelialization (%). The area stenosis with the DES 8 was found to be 30±13% and the rate of endothelialization exhibited by the DES 8 was found to be 100%, showing that injuries to the inner wall of vessels, which occurred at the time of placement of the stents, were completely repaired. The area stenosis exhibited by the "Cypher" stents was found to be 54±22% and the rate of endothelialization thereof was found to be 95%.

With the stents of the present invention, which has a capability of achieving a sustained release of the drug, the vascular endothelia was completely repaired one month after the implantation of the stent in the miniature pig, but with the "Cypher" stents a part of the inner wall of vessels was not covered with the endothelial cells even three months after the implantation of the stent.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A method of inhibiting vascular intimal hyperplasia using a stent having a stent body of a cylindrical configuration having outer and inner surfaces with a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:
   controlling the rate of release of argatroban from the stent in phosphate buffered saline at 37° C., which is measured on the first day and the second day subsequent to immersion of the stent in the phosphate buffered saline, to be 3 $\mu g/cm^2$ per day or higher by selecting a predetermined thickness of the second coated layer so as to fall within the range of 0.5 to 5.0 microns;
   placing the stent within a blood vessel; and
   wherein argatroban is released from the stent, thereby inhibiting the vascular intimal hyperplasia without inhibiting proliferation of endothelial cells.

2. A method of inhibiting vascular intimal hyperplasia using a stent having a stent body of a cylindrical configuration having outer and inner surfaces with a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:
   controlling the rate of release of argatroban from the stent in phosphate buffered saline at 37° C., which is measured on the second day subsequent to immersion of the stent in that phosphate buffered saline, to be a value within the range of 3-100 $\mu g/cm^2$ per day or higher by selecting a predetermined thickness of the second coated layer so as to fall within the range of 0.5 to 5.0 microns;
   placing the stent within a blood vessel; and
   wherein argatroban is released from the stent, thereby inhibiting the vascular intimal hyperplasia without inhibiting proliferation of endothelial cells.

3. A method of inhibiting vascular intimal hyperplasia using a stent having a stent body of a cylindrical configuration having outer and inner surfaces with a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:
   controlling the rate of release of argatroban from the stent in phosphate buffered saline at 37° C., which is measured on the third to seventh day subsequent to immersion of the stent in that phosphate buffered saline, to be a value within the range of 2-50 $\mu g/cm^2$ per day or higher by selecting a predetermined thickness of the second coated layer so as to fall within the range of 0.5 to 5.0 microns;
   placing the stent within a blood vessel; and
   wherein argatroban is released from the stent, thereby inhibiting the vascular intimal hyperplasia without inhibiting proliferation of endothelial cells.

4. The method of inhibiting vascular intimal hyperplasia according to claim 1, wherein the rate of release of argatroban contained in the first composition is controlled by micro dispersing the argatroban in the polymer.

5. The method of inhibiting vascular intimal hyperplasia according to claim 2, wherein the rate of release of argatroban contained in the first composition is controlled by microdispersing the argatroban in the polymer.

6. The method of inhibiting vascular intimal hyperplasia according to claim 3, wherein the rate of release of argatroban contained in the first composition is controlled by microdispersing the argatroban in the polymer.

7. The method of inhibiting vascular intimal hyperplasia according to claim 1, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

8. The method of inhibiting vascular intimal hyperplasia according to claim 2, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

9. The method of inhibiting vascular intimal hyperplasia according to claim 3, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

10. The method of inhibiting vascular intimal hyperplasia according to claim 1, wherein the polymer used to form the second coated layer is poly(lactic acid-glycolic acid) and wherein the rate of release of argatroban is controlled by changing the copolymerization ratio between the lactic acid and the glycolic acid.

11. The method of inhibiting vascular intimal hyperplasia according to claim 2, wherein the polymer used to form the second coated layer is poly(lactic acid-glycolic acid) and wherein the rate of release of argatroban is controlled by changing the copolymerization ratio between the lactic acid and the glycolic acid.

12. The method of inhibiting vascular intimal hyperplasia according to claim 3, wherein the polymer used to form the second coated layer is poly(lactic acid-glycolic acid) and wherein the rate of release of argatroban is controlled by changing the copolymerization ratio between the lactic acid and the glycolic acid.

13. A method of inhibiting vascular intimal hyperplasia, comprising: placing a stent within a blood vessel, the stent having a stent body of a cylindrical configuration having outer and inner surfaces with a diamond-like thin film coated on the surfaces, a first coated layer coating at least the outer surface of the stent body, wherein the first coated layer is prepared of a first composition comprising a biodegradable polymer and a vascular intimal hyperplasia inhibitor of a kind, comprising argatroban, which does not inhibit proliferation of endothelial cells, the weight compositional ratio of the polymer to the vascular intimal hyperplasia inhibitor being within the range of 8:2 to 3:7, and a second coated layer coating substantially completely over the first coated layer; and wherein argatroban is released from the stent, thereby inhibiting the vascular intimal hyperplasia without inhibiting proliferation of endothelial cells.

14. A method of inhibiting vascular intimal hyperplasia using a stent having a stent body of a cylindrical configuration having outer and inner surfaces without a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:

controlling the rate of release of argatroban from the stent in phosphate buffered saline at 37° C., which is measured on the first day and the second day subsequent to immersion of the stent in the phosphate buffered saline, to be 3 $\mu g/cm^2$ per day or higher by selecting a predetermined thickness of the second coated layer so as to fall within the range of 0.5 to 5.0 microns;

placing the stent within a blood vessel; and wherein argatroban is released from the stent, thereby inhibiting the vascular intimal hyperplasia without inhibiting proliferation of endothelial cells.

15. A method of inhibiting vascular intimal hyperplasia using a stent having a stent body of a cylindrical configuration having outer and inner surfaces without a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:

controlling the rate of release of argatroban from the stent in phosphate buffered saline at 37° C., which is measured on the second day subsequent to immersion of the stent in the phosphate buffered saline, to be a value within the range of 3-100 $\mu g/cm^2$ per day or higher by selecting a predetermined thickness of the second coated layer so as to fall within the range of 0.5 to 5.0 microns;

placing the stent within a blood vessel; and wherein argatroban is released from the stent, thereby inhibiting the vascular intimal hyperplasia without inhibiting proliferation of endothelial cells.

16. A method of inhibiting vascular intimal hyperplasia using a stent having a stent body of a cylindrical configuration having outer and inner surfaces without a diamond-like thin film coated on the surfaces, a first coated layer coating at least the outer surface of the stent body, the first coated layer being prepared of a first composition comprising a biodegradable polymer and a vascular intimal hyperplasia inhibitor of a kind, comprising argatroban, which does not inhibit proliferation of endothelial cells, the weight composition ratio of the polymer to the vascular intimal hyperplasia inhibitor being within the range of 8:2 to 7:3, and a second coated layer coating substantially completely over the first coated layer, the method comprising:

controlling the rate of release of argatroban from the stent in phosphate buffered saline at 37° C., which is measured on the third to seventh day subsequent to immersion of the stent in the phosphate buffered saline, to be a value within the range of 2-50 $\mu g/cm^2$ per day or higher by selecting a predetermined thickness of the second coated layer so as to fall within the range of 0.5 to 5.0 microns;

placing the stent within a blood vessel; and wherein argatroban is released from the stent, thereby inhibiting the vascular intimal hyperplasia without inhibiting proliferation of endothelial cells.

17. The method of inhibiting vascular intimal hyperplasia according to claim 14, wherein the rate of release of argatroban contained in the first composition is controlled by micro-dispersing the argatroban in the polymer.

18. The method of inhibiting vascular intimal, hyperplasia according to claim 15, wherein the rate of release of argatroban contained in the first composition is controlled by micro-dispersing the argatroban in the polymer.

19. The method of inhibiting vascular intimal hyperplasia according to claim 16 wherein the rate of release of argatroban contained in the first composition is controlled by micro-dispersing the argatroban in the polymer.

20. The method of inhibiting vascular intimal hyperplasia according to claim 14, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

21. The method of inhibiting vascular intimal hyperplasia according to claim 15, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

22. The method of inhibiting vascular intimal hyperplasia according to claim 16, comprising: dissolving the first composition in a solvent selected from the group consisting of a mixture of lower alkylketone and methanol, and a mixture of lower alkyl ester and methanol; coating a surface of the stent body with the formed solution; and then removing the mixed solvent to produce the first layer which controls the release rate of argatroban.

23. The method of inhibiting vascular intimal hyperplasia according to claim 14, wherein the polymer used to form the second coated layer is poly(lactic acid-glycolic acid) and wherein the rate of release of argatroban is controlled by changing the copolymerization ratio between the lactic acid and the glycolic acid.

24. The method of inhibiting vascular intimal hyperplasia according to claim 15, wherein the polymer used to form the second coated layer is poly(lactic acid-glycolic acid) and wherein the rate of release of argatroban is controlled by changing the copolymerization ratio between the lactic acid and the glycolic acid.

25. The method of inhibiting vascular intimal hyperplasia according to claim 16, wherein the polymer used to form the second coated layer is poly(lactic acid glycolic acid) and wherein the rate of release of argatroban is controlled by changing the copolymerization ratio between the lactic acid and the glycolic acid.

26. A method of inhibiting vascular intimal hyperplasia, comprising: placing a stent within a blood vessel, the stent comprising; a stent body of a cylindrical configuration having outer and inner surfaces without a diamond-like thin film coated on the surfaces, a first coated layer coating at least the outer surface of the stent body wherein the first coated layer is prepared of a first composition comprising a biodegradable polymer and a vascular intimal hyperplasia inhibitor of a kind, comprising argatroban, which does not inhibit proliferation of endothelial cells, the weight compositional ratio of the polymer to the vascular intimal hyperplasia inhibitor being within the range of 8:2 to 3:7, and a second coated layer coating substantially completely over the first coated layer; and wherein argatroban is released from the stent, thereby inhibiting the vascular intimal hyperplasia without inhibiting proliferation of endothelial cells.

* * * * *